United States Patent
Sovak et al.

(10) Patent No.: US 6,472,415 B1
(45) Date of Patent: *Oct. 29, 2002

(54) ANDROGEN RECEPTOR SUPPRESSORS IN THE THERAPY AND DIAGNOSIS OF PROSTATE CANCER, ALOPECIA AND OTHER HYPER-ANDROGENIC SYNDROMES

(75) Inventors: Milos Sovak, La Jolla; Allen L. Seligson, San Marcos; James Gordon Douglas, III, San Diego; Brian Campion, Leucadia; Jason W. Brown, San Diego, all of CA (US)

(73) Assignee: Biophysica, Inc., La Jolla, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/502,376

(22) Filed: Feb. 11, 2000

Related U.S. Application Data (63) Continuation-in-part of application No. 09/215,351, filed on Dec. 18, 1998.

(51) Int. Cl.[7] .................... A61K 31/415; A61K 31/275; C07D 233/72; C07D 233/88
(52) U.S. Cl. .................... 514/398; 514/520; 548/320.1; 548/321.1; 558/413
(58) Field of Search ................ 514/520, 398; 548/320.1, 321.1; 558/413

(56) References Cited

U.S. PATENT DOCUMENTS

| | | |
|---|---|---|
| 4,636,505 A | 1/1987 | Tucker |
| 4,880,839 A | 11/1989 | Tucker |
| 5,656,651 A | 8/1997 | Sovak et al. |

FOREIGN PATENT DOCUMENTS

| | | |
|---|---|---|
| EP | 0 100 172 | 8/1983 |
| WO | WO 97/00071 | 1/1997 |

OTHER PUBLICATIONS

Battmann et al., *J. Steroid Biochem. Molec. Biol.* (1998), 64:103–11.
Battmann et al., *J. Steroid Biochem. Molec. Biol.* (1994), 48:55–60.
Brouwer et al., *J. of Dermatology* (1997), 137:699–702.
Cousty–Berlin, *J. Steroid Biochem. Molec. Biol* (1994), 51:47–55.
Tucker, et al., "Nonsteroidal antiandrogens. Synthesis and structure–activity relationships of 3–substituted derivatives if 2–hydroxypropionanilides," J. of Medicinal Chemistry, vol. 31, No. 5, May 1988.
Tucker, et al., "Resolution of the nonsteroidal antiandrogen 4'–cyano–3–u(4–fluorophenyl)sulfonyl–2–hydroxy–2–methyl–3'–(trifluoromethyl)–propionanilide and the determination of the absolute configuration of the active enantiomer," J. of Medicinal Chemistry, vol. 31, No. 4, Apr. 1988.
Kaufman, *Dermatologic Clinics* (1996), 14:697–711.
Kondo, et al., "Relative Potency of Antiadnrogens..."(1996), 146–52.
Kuil, et al. *European Urology* (1996), 29:78–82.
Shapiro, et al., *Dermatologic Clinics* (1998), 16:341–356.
Simard, et al., *Adult Urology* (1997), 49:580–9.
Toney, et al., *Steroid Biochem. Molec. Biol.* (1997), 60:131–6.

Primary Examiner—Floyd D. Higel
Assistant Examiner—Ebenezer Sackey
(74) Attorney, Agent, or Firm—Jeffrey M. Libby; Barbara Rae-Venter; Rae-Venter Law Group, P.C.

(57) ABSTRACT

Substituted phenylalanines are provided comprising an hydantoin, urea or 2-hydroxyl, 2-methylpropionyl group, dimers thereof and alkyl, polyfluoroamido and haloarylamino derivatives thereof, as well as radiolabeled derivatives thereof. The compounds bind specifically to the androgen receptor and find use in indications associated with the androgen receptor, such as cell hyperplasia dependent on androgens, hirsutism, acne and androgenetic alopecia.

35 Claims, 2 Drawing Sheets

ANDROGEN RECEPTOR SUPPRESSORS IN THE THERAPY AND DIAGNOSIS OF PROSTATE CANCER, ALOPECIA AND OTHER HYPER-ANDROGENIC SYNDROMES

This application is a Continuation-in-Part of copending prior application U.S. Ser. No. 09/215,351, filed on Dec. 18, 1998, the disclosure of which is incorporated herein by reference.

INTRODUCTION

Technical Field

The field of this invention is compounds and their use in the treatment of prostate cancer and hyper-androgenic syndromes including alopecia, hirsutism and acne vulgaris.

Background

The existence of a number of pathologic syndromes depends on androgen hormones. Thus, growth of prostate cancer in early stages is androgen driven and can, at least temporarily, be stopped by androgen deprivation. Androgenic alopecia is caused by an unexplained switch from the growth promoting effect of androgens on the hair follicles to hair loss. In skin androgen mediated disorders, such as alopecia, acne vulgaris, and hirsutism, excess of the cutaneous androgens were shown to be the major nosological factor.

The pathophysiology of both male and female hair loss is not yet fully understood and the therapy is unsatisfactory. Factors ranging from low scalp blood flow, deficiency of nutrients and hair-related vitamins, microbially-driven inflammatory changes, etc., have been considered. It is nevertheless, apparent that the most influential factor is the effect of the androgenic hormones (AH) on the scalp hair follicles. AH are important in the physiology of skin; they promote the growth of the beard and of the body hair throughout life. The growth of the scalp hair also depends on AH but only in early life. It is not yet explained why AH, with increasing age, switch from promoting growth of the scalp hair to its loss, inducing conditions known as an androgenic effluvium (AE) and alopecia (AGA). In hirsutism and acne vulgaris, excess of cutaneous AH was shown to be the major factor in those complex syndromes.

The androgenic hormones can act only via an androgenic receptor (AR), which is a transcription factor, a protein which interacts with a specific region of DNA. Thus, the mode of action of testosterone and its much more potent analog, 5-alpha dihydrotestoterone (DHT) depends upon binding to the AR. Only then can transcription by RNA polymerase II take place. AH are derived either from the systemic circulation and/or synthesized in synthesized in the skin bind to the AR located in the hair follicles.

In the treatment of androgenic alopecia, various antiandrogens originally developed for the treatment of prostate cancer were claimed for systemic use, but side effects of chronic therapy with these systemically absorbable substances were of concern. In cutaneous afflictions anti-androgenic compositions have been tried, but with limited success, possibly because all non-steroidal compounds are resorbed by the skin and elicit systemic effects, which prevents their use in males. In the scalp, the precursors to androgens are normally converted into potent androgens, which bind to the AR in the hair follicles and promote hair growth. In genetically pre-disposed subjects however androgens at certain age cause hair loss. Clearly, a topically active composition capable of cutaneous, but not systemic resorption, and of suppressing or eliminating the AR locally, would be useful in preventing or reversing the incipient androgenic alopecia.

The current state of prostate cancer therapy (CaP), the second most prevalent malignancy in males, is unsatisfactory. When detected early, with the tumor strictly confined to the prostate gland, CaP can be often controlled by implantation of radioactive seeds, or by prostatectomy, which often results in incontinence and impotence. Locally advanced prostate cancer can often be reasonably controlled when in the pelvis and is encompassed into a single port of an external radiation beam.

For advanced CaP, the standard treatment is androgen receptor-blockade, usually in combination with LHRH superagonists, which suppresses both adrenal and testicular testosterone. The rationale of this approach is that early prostate cancer invariably depends on androgens for growth. The activity mechanism of clinically utilized antiandrogens is thought to involve blockade of the AR by binding to it and/or by interference with binding of the AR to the DNA; some agonistic compounds can even promote DNA binding but they do modify the binding domain. Thus, cyproterone acetate was found to block about 50% of AR binding to the DNA, while flutamide, bicalutamide or nilutamide, were found to completely block such binding. All of these state of the art compositions have nevertheless only limited applicability, as the primary tumor and its metastases eventually become hormonally refractory and resistant to further anti-androgenic therapy. The reason is invariably AR mutation, which can be occasionally found as a genetic deviation, but is usually a result of the AR blockade. Even when both suprarenal and testicular androgens are eliminated by chemical castration, using LHRH super agonist and/or by surgical castration, the mutated receptor retains the capability to be activated by various steroidal metabolites and even progestins and estrogens. A variety of other factors can activate the androgen receptor gene via AR activation, such as insulin-like growth factor, epidermal growth factor, and keratinocyte growth factor and neuroendocrine transmitters, such as serotonin. Therefore, blocking the AR is not an ideal treatment and a new approach is needed. It has also been shown that as a result of the AR blockade, the AR gene is amplified with the resulting overproduction of the AR. In 6 to 24 months the AR mutates and the tumor and metastases became hormone refractory and continue to grow.

The common denominator of resistance to current antiandrogens is a modification of the AR. Even after a relapse following androgen blockade therapy, experiments indicate the AR is still present and plays a major role in the propagation of CaP cells.

In selecting therapeutic options, a correct therapeutic decision can only be made if the extent of the disease is known. When CaP is confined strictly t the gland, surgery and/or local or external radiation can be curative. However, in the case of extracapsular disease, prostatectomy or radiation are not only useless, but noxious, since a high rate of serious side effects, such as impotence, incontinence and chronic inflammation of the adjacent tissues accompanies these interventions. Members of the current diagnostic armamentarium comprise digital rectal palpation, serum prostate specific antigen determination and ultrasound, magnetic resonance or x-ray imaging. These techniques cannot reliably detect CaP spread into the soft tissues. Thus, metastases to the lymph nodes cannot be reliably detected with these methods resulting in clinical understaging of 40 to 60% of the instances.

The prior art of diagnostic localizing agents for CaP teaches specific radioactively labeled antibodies, but widespread use is limited by the complexity of the procedure. 5α-dihydrotestosterone labeled with $^{18}F$ has been used for PET scanning, a generally inaccessible imaging modality.

There are, therefore, substantial deficiencies in both therapeutic and diagnostic approaches to the treatment of CaP. It is therefore of interest to find compounds which not only block the AR, but also diminish the number of ARs which are available. In addition, another desirable characteristic for topical purposes would be compounds which have low or no systemic resorption. Also, the compounds should degrade or be metabolized into components of low or no toxicity and have little or no anti-androgenic activity. In addition, radioisotope labeled compounds specific for neoplastic prostate cells would be of great help. These compounds would allow the physician to visualize the pathomorphology of CaP accurately, so that unnecessary and costly surgery and/or radiation is avoided in patients where CaP has progressed beyond the reach of curative surgery or the scope of a single radiation port. Other appropriate therapies, such as androgen ablation and/or unspecific chemotherapy, can then be instituted.

Systemic antiandrogens (AA) are orally administered in vivo stable compounds known to block the AH binding to AR. Originally developed for the treatment of prostate cancer, these compounds have considerable general effects since they block AR systemically, resulting among others, in loss of libido and male sexual function. The nonsteroidal agents cannot be used in males for the AE or AGA treatment at all, neither orally nor topically, since they are well absorbed from the skin and are stable in vivo. Attempts to treat male EA and AGA with topical steroidal AA such as cyproterone acetate, chlormadimone acetate and spironolactone were not successful, apparently because of poor absorption into the skin (Zaumseil, R-P.: Schering AG/Asche Corp., Hamburg Personal Communication 1997). Some antiandrogens also have a skin irritation potential.

Systemic AA were proposed for treatment of women suffering with AE and AGA (Diamanti-Kandarakis, E. Current aspects of antiandrogen therapy in women. *Current Pharm Des*, Sep. 5, 1999(9): 707–23), but concerns for side effects call for clinical studies. It is generally known, at least in males, that extended AR blockade leads to AR mutation, and that the mutated receptor attains the capability to be activated by other substances such as various steroidal metabolites and even progestins and estrogens, insulin-like growth factor, epidermnal growth factor and keratinocyte growth factor and neuroendocrine transmitters such as serotonin. It has also been shown that the AR blockade amplifies the AR gene. It is therefor apparent that treatment of hair loss in women by blocking AR with systemic AA is not ideal and that in men it is not acceptable at all.

Currently available for treatment of AE and AGA are the topical Minoxidil and its derivatives, and the oral finasteride (Scow, D. T.; Nolte, R. S.; Shaughnessy, A. F. Medical treatments for balding in men. *American Family Physician*, Apr. 15, 1999, 59(8): 2189–94, 2196). Minoxidil, an antihypertensive drug, has incidentally shown to prevent hair loss, and to an extent promote regrowth, but only in the vertex scalp, the activity is tentatively explained by activation of the prostaglandin endoperoxide synthase-1, increase for the local blood flow, suppression of bacterial infection and/or by a modification of the AH metabolism in the dermal papilla. (Michelet, J. F.; Commo, S.; Billoni, N.; Mah, Y. F.; Bernard, B. A. Activation of cytoprotective prostaglandin synthase-1 by minoxidil as a possible explanation for its hair growth-stimulating effect. *Journal of Investigative Dermatology*, February 1997, 109(2): 205–9; Pirard-Franchimont, C.; DeDoncker, P.; Cauwenbeergh, G.; Pirard, G. E.: Ketoconazole shampoo: effect of long-term use in androgenic alopecia. *Dermatology*, 1998; 196 (4): 474–7; Sato, T.; Tadokoro, T.; Soroda, T.; Asada, Y.; Itami, S.; Takayasu, S. Minoxidil increases 17 beta-hydroxysteroid dehydrogenase and 5 alpha-reductase activity of cultured human dermal papilla cells from balding scalp. *Journal of Dermatological Science*, Feb. 19, 1999(2): 123–5).

Finasteride taken orally and daily suppresses conversion of testosterone into dihydrotestosterone (DHT), thus lowering AH activity in the scalp. The studies indicate about half of the men achieve slight to moderate improvement in the anterior mid scalp and in approximately one-half, the effluvium is arrested. Side effects include decreased libido and erectile function, which disappear after drug withdrawal. (Kaufman, K. D.; Olsen, E. A.; Whiting, D.; Roberts, J. L.; Hordinsky, M.; Shapiro, J.; Binkowitz, B.; Gormley, G. J. Finasteride in the Treatment of Men with Androgenic Alopecia. Finasteride Male Pattern Hair Loss Study Group. *Journal of the American Academy of Dermatology.* October 1998, 39 (4 Pt. 1): 578–89). No studies are yet available to prove whether such a long term systemic manipulation is hormonal balance is harmless.

Clearly a topically active antiandrogen suppressing rather than blocking the cutaneous AR, while not irritating and not systemically absorbable would be useful in the therapy of AH dependent cutaneous afflictions.

We designed and synthesized a number of novel compounds with potential antiandrogen activity and unexpectedly found that some, rather than blocking suppressed the AR, by a concentration and time dependent fashion. (Sovak, M. S.; Bressi, J. C.; Douglas, J.; Campion, B.; Wrasidlo, W. Androgenic Directed Compositions, U.S. application Ser. No. 09/215,351, 1998) Some of these compounds showed extremely low or no systemic bioavailability upon topical application. Furthermore, BP-766 proved to be biodegradable into components devoid of antiandrogenic activity and having low systemic toxicity. The topically active and not systemically absorbable suppressor of cutaneous androgen receptors is described herein. It offers a sound therapeutic concept in androgenic effluvium and alopecia, both in males and females.

Relevant Literature

U.S. Pat. No. 5,656,651 and WO97/00071, and references cited therein, describe anti-androgenic directed compositions based on phenyldimethylhydantoins, where the phenyl group is substituted with a trifluoromethyl group and either a cyano or nitro group. See also, Battmann et al., J. Steroid Biochem. Molec. Biol. 64:103–111 (1998); Cousty-Berlin, ibid 51:47–55 (1994); and Battmann et al., ibid 48:55–60 (1994), for a description of analogous compounds and their activity. For other compounds having the substituted phenyl moiety, see U.S. Pat. Nos. 4,636,505 and 4,880,839, and EP 0 100 172. For discussions about the activities of antiandrogens, see Kuil and Brinkmann, Eur. Urol. 29:78–82 (1996); Kondo et al., Prostate 29:146–152 (1996), and Simard, et al., Urology 49:580–589 (1997). For discussions about alopecia and its relationship with androgens, see Kaufman, Dermatologic Clinics 14:697–711 (1996); Toney et al., J. Steroid Biochem. Molec. Biol. 60:131–136 (1997); Brouwer et al., J. of Dermatology 137:699–702 (1997); and Shapiro and Price Dermatologic Clinics 16:341–356 (1998).

SUMMARY OF THE INVENTION

Compositions and their method of use are provided, where the compositions are substituted-phenyl-2-methyl,2-(hydroxy or methyl)-3-heteroatom substituted-propionamide derivatives, having heterolinked perfluoroacyl or haloaryl substituents or being bis-derivatives, where the substituent group may be linked to the heteroatom directly or by a linking group. The compounds are active anti-androgenic compounds and find use in the treatment of neoplasms and alopecia dependent on androgen hormones. In addition, the compounds may be radioisotope labeled for use in therapy and diagnosis.

DESCRIPTION OF THE SPECIFIC EMBODIMENTS

Compositions are provided which are characterized by having an aniline group which has at least one substituent at the para position, desirably a second substituent at the meta position, and to which the aniline nitrogen is bonded a 2-methyl,2-(hydroxy or methyl)-3-heteroatom substituted-propionyl or N-substituted carbamoyl, particularly thiocarbamoyl. The heteroatom (including the nitrogen of the carbamoyl group) is linked through a bond or linking group to a perfluoroacyl, haloaryl, or alkyl substituent or to a divalent linking group to form a bis-compound. The compounds have individual or collective characteristics associated with cellular toxicity, diminution of androgen receptors on the surface of cells and low systemic resorption when administered topically. In addition, the compounds may be radioisotope labeled, to be used in diagnosis and therapy.

The monomeric compounds will generally be of from at least 12 carbon atoms, usually at least 14 carbon atoms, more usually of at least 16 carbon atoms and not more than about 36 carbon atoms, usually not more than about 28 carbon atoms, while the bis-compounds will usually be at least 20 carbon atoms, usually at least 22 carbon atoms and not more than about 40 carbon atoms, usually not more than about 36 carbon atoms.

The two position of the propionamide has two methyl groups or one methyl and one hydroxy group. The perfluoroacyl group will be linked to the 3-heteropropionamide through the heteroatom by a bond or a linking group of from 1 to 10, usually 2 to 8 carbon atoms and from 0 to 6, usually 0 to 4, more usually 0 to 2 heteroatoms in the chain of the linking group. The linking group may be aliphatic, alicyclic, heterocyclic or aromatic, usually aliphatic, more usually saturated aliphatic.

For the most part, the compounds of this invention will have the following formula:

wherein:

Q is chalcogen (oxygen or sulfur);

X is nitro (NO$_2$), cyano (CN), or halogen, particularly of from atomic no. 9 to 35, particularly 9 to 17 (fluorine and chlorine);

V is CF$_3$, halogen, particularly of from atomic no. 9 to 35, particularly 9 to 17 (fluorine and chlorine) or H; usually CF$_3$;

T is hydrogen or is taken together with T$^1$ to form a C=Z bridge, where Z is chalcogen of atomic number 8 to 16 (oxygen {carbonyl} or sulfur {thiocarbonyl}), particularly sulfur;

W is OH when T is H and methyl when T and T$^1$ are C=Z;

U is N when T and T$^1$ are taken together to form a C=Z bridge or when d is 0, and is otherwise taken together with T$^1$ to form a bond or NH, S or O, particularly NH and S;

n is 1 or 2 and d is 0 or 1;

when d is 0, T and T$^1$ are hydrogen;

when d is 1, then:

when n is 1, Y is a bond or linking group of from 1 to 10, frequently 0 to 8 carbon atoms, usually 2 to 8, more usually 2 to 6 carbon atoms and from 0 to 6, usually 0 to 4 heteroatoms, with from 0 to 4 heteroatoms in the chain, where the heteroatoms are N, O, S, and the heteroatoms are present as amino (includes amido), oxy and oxo- and non-oxo-carbonyl, and thio and thiono- and non-thiono-carbonyl, where the linking group may be aliphatic, alicyclic, heterocyclic or aromatic, usually aliphatic, usually saturated; and Z, when not taken together with Y, is an aliphatic group of from 1 to 10, usually 1 to 6, more usually 1 to 5 carbon atoms, saturated or unsaturated, e.g. double or triple bond, polyfluoroacylamido group of from 2 to 10, frequently of 2 to 8, usually 2 to 6, more usually 3 to 5 carbon atoms and having at least 2 fluoro groups and a total of 2m-1 fluoro groups, usually having at least 2m-2 fluoro groups, wherein m is the number of carbon atoms, or substituted arylamino of from 6 to 12, more usually 6 to 10 carbon atoms, particularly anilino, and halogen of atomic number from 9 to 80, particularly F, Cl, Br and I, more particularly Br and I (atomic no. 35 to 80), particularly para substituted;

when n is 2, Y and Z are taken together to form a bond or a linking group of a total of from 1 to 10, usually 1 to 8 atoms, having 0 to 10, usually 0 to 8 carbon atoms, more usually 2 to 6 carbon atoms and from 0 to 6, usually 0 to 4 heteroatoms, with from 0 to 4, usually 0 to 2, heteroatoms in the chain, where the heteroatoms are N, O, S, there being at least one carbon atom or heteroatom in the linking group, and the heteroatoms are present as amino (includes amido), oxy and oxo- and non-oxo-carbonyl, and thio and thiono- and non-thiono-carbonyl, where the linking group when other than 1 heteroatom may be aliphatic, alicyclic, heterocyclic or aromatic, usually aliphatic, usually saturated; and the phenyl group, Y and/or Z may be substituted with convenient radiolabel, particularly Z, where the label may be radioactive iodine, chelated technetium, or other suitable emitter.

When Y is a bond, U will also usually be a bond, so as to join the nitrogen of the polyfluoroacylamido or anilino group to the propionyl carbon atom.

For radiolabeling, Z may have different convenient functionalities depending on the nature of the radiolabel. For example, with radioactive iodine, one may use an acetylenic group for addition a hydride, e.g. a tin hydride, followed by substitution of the tin group with iodine. Where the radiolabel is chelated, the chelating group may be attached to Z by any convenient functionality, such as an amide group, ester, ether, thioether, amino, etc. Chelating compounds include combinations of imidazoles, thiolacetic acids, cysteine, glycineamides, etc.

The compounds may or may not have one or more stereoisomeric centers. The compounds may be used as racemic mixtures or be resolved in their enantiomers and used as enantiomers.

When the compounds have the hydantoin ring, they will usually come within the following formula:

wherein:

$X^1$, $V^1$, and $Y^1$ come within the definitions of X, V and Y, respectively;

$Y^1$ is usually alkylene of from 2 to 10, usually 2 to 8, more usually 2 to 6, carbon atoms;

$A^1$ is chalcogen (oxygen or sulfur), particularly sulfur; and $Z^1$ is a polyfluoroacylamido of from 2 to 10, usually 2 to 6, more usually 3 to 5 carbon atoms and having at least 2 fluoro groups and not more than 2m-1 fluoro groups, usually having at least 2m-2 fluoro groups, wherein m is the number of carbon atoms, or substituted arylamino of from 6 to 12, more usually 6 to 10 carbon atoms, particularly anilino, and halogen of atomic number from 9 to 80, particularly F, Cl, Br and I, more particularly Br and I (atomic no. 35 to 80) preferably para-substituted.

Those compounds which have an 2-hydroxy, 2-methylpropionyl group as a moiety will for the most part have the following formula:

wherein:

$X^2$, $V^2$ and $n^2$ come within the definitions of X, V and n, respectively;

$U^2$ is a bond or heteroatom, particularly nitrogen and chalcogen (O and S); when $n^2$ is 1;

$Y^2$ is an alkylene group of from 1 to 10, usually 1 to 6 carbon atoms, more usually 2 to 6 carbon atoms and 0 to 4 heteroatoms, which heteroatoms are N and chalcogen and include the functional groups carbonyl, thiocarbonyl, oxy, thio, and amino; and $Z^2$ is a polyfluoroacylamido of from 2 to 10, usually 2 to 6, more usually 2 to 4 carbon atoms and having at least 2 fluoro groups and not more than 2m-1 fluoro groups, usually having at least 2m-2 fluoro groups, or substituted arylamino of from 6 to 12, more usually 6 to 10 carbon atoms, particularly phenyl, and halogen of atomic number from 9 to 80; particularly F, Cl, Br and I, more particularly Br and I, preferably para substituted.

The compounds which have the carbamoyl group, will for the most part have the following formula:
wherein:

$X^3$ and $V^3$ come within the definitions of $X^1$ and $V^1$;

$Q^3$ is chalcogen, particularly sulfur;

$Y^3$ is a bond or alkylene group of from 1 to 6, usually 1 to 3 carbon atoms;

$Z^3$ is alkyl of from 1 to 6 carbon atoms, a polyfluoroacylamido of from 2 to 10, usually 2 to 6, more usually 2 to 4 carbon atoms and having at least 2 fluoro groups and not more than 2m-1 fluoro groups, usually having at least 2m-2 fluoro groups, or substituted arylamino of from 6 to 12, more usually 6 to 10 carbon atoms, particularly phenyl, and halogen of atomic number from 9 to 80, particularly F, Cl, Br and I, more particularly Br and I, preferably para substituted.

The subject compounds can be prepared in accordance with conventional ways, varying the particular procedure based on the particular side groups. The preparation of hydantoins conveniently involves the use of an isocyanate and a substituted α-aminoacetonitrile. By appropriate choice of the isocyanate and the α-aminoacetonitrile, one may arrive at the final product in a single step. Alternatively, one may employ various protective groups, which may be subsequently removed or provide for substituents which become involved in the formation of the hydantoin or may provide for sites for further derivatization. Various procedures are described in EPO Publication nos. 0 494 819 and 0 580 459. The urea compounds may be prepared using an isocyanate (including thioisocyanate) and an amino compound. A significant number of examples are provided for the hydantoins and the propionyl moiety compounds in the experimental section of this application.

The subject compounds can be used as antiandrogens, substituting for known antiandrogens in the treatment of proliferative diseases, hirsutism, acne and androgenetic alopecia. The subject compounds display one or more of the following properties: specific binding and high affinity to the androgen receptor; destroying or suppressing the presence of the androgen receptor in a concentration dependent fashion; low or no systemic resorption when applied topically; and limited stability, degrading into components of low toxicity and no androgenic activity. The subject compounds may be used individually or in combination and with other antiandrogens or other treatments, such as flutamide, bicalutamide and nilutamide, irradiation, heat, or the like, as may be conventionally employed and as may be moderated for use in conjunction with the subject compounds. The treatments may be performed concurrently, consecutively or in accordance with a predetermined regimen to minimize the likelihood of neoplastic cell refractoriness.

The subject compounds are found to have high cytostatic and cytotoxic activity, inhibiting cell growth and viability of cells having an androgen receptor. They also have substantially greater effect against neoplastic cells, as compared to normal cells.

Therapeutic compositions can be formulated in accordance with conventional ways and the indication to be treated. The composition may be formulated for oral or parenteral, e.g. intravascular, subcutaneous, intratumoral, intraperitoneally, etc., administration, as a pill, powder, capsule, aqueous or oily solution or dispersion, or the like. Conventional carriers include saline, phosphate buffered saline, water, vegetable oils, ethanol, isopropanol, etc. Excipients, buffers, stabilizers, flavorings or the like may be employed. The concentration may be from about 0.1 to 10 weight % and at a dosage in the range of about 0.1 mg to about 5 g, usually not more than about 2 g/dose. One or more doses may be given daily.

The subject compounds may be used in conjunction with conventional therapeutic agents for a specified treatment, being used in combination with anti-neoplastic agents, agents for the treatment of alopecia, etc. Of particular interest is to employ a regimen where the subject compound is used with an agent for treating alopecia, such as Minoxidil7 or Aminexil7 (a trademark of L=Oreal), where the dosage employed for the known agent may be the same as in the absence of the subject compound or may be reduced based on the observed experience with the combination. Determining the optimum dosage for the combination can be done in conventional ways using appropriate clinical studies and varying ratios of the two ingredients, which may be in a common formulation or employed as two independent formulations.

The subject compounds may be used in competitive assays or as controls for evaluating other compounds as to their cytostatic or cytotoxic effect or for blocking the androgen receptor. Thus, specific cell lines may be employed where the effect of an agent on the activity of a subject compound may be determined in relation to the survival rate or other indicia of the target cells. Also, in mixtures of cells containing neoplastic androgenic receptor containing cells, the subject compounds can be used to eliminate the neoplastic cells in the presence of normal cells. Thus, in a variety of cultures, where androgenic receptor containing cells may be susceptible to becoming or are tumorous, by maintaining a cytotoxic level of a subject compound in the medium, cells may be selectively killed.

In addition, the radiolabeled compounds may be used for therapeutic and/or diagnostic purposes, depending upon the choice of radiolabel. The radiolabeled compounds may be formulated in accordance with conventional ways using physiologically acceptable components, exemplified by various liquid dispersants, such as deionized water, PBS, DMSO, ethanol, etc. in conjunction with various additives, e.g. non-ionic detergents, dextrose, stabilizers, antibiotics, etc. Normally, the radioactive label will be provided immediately prior to use, so that the radioactive product will be prepared at the site or be shipped to the site of the injection. The formulation will normally be administered by intravenous injection.

The following examples are offered by way of illustration and not by way of limitation.

Experimental

EXAMPLES

Example 1

4-nitro-3-trifluoromethyl-N-(2-hydroxy-2-methyl-3-aminopropionyl)aniline. (BP-34)

A pressure reactor was charged with 4-nitro-3-trifluoromethyl-N-[2,3-epoxy-2-methyl propionyl]aniline, BP-33, (10.0 g, 34.46 mmol) (see FIG. 3) and methanol (100 mL). After cooling to −70° C., ammonia in excess was condensed into the reactor which was sealed and stirred 14 hours. Following evaporation, the crude solid was washed with cold $CH_2Cl_2$ (50 mL). Filtration and drying gave 6.1 g BP-34 (58% yield).

Melting point: 142–145° C.

Example 2

4-nitro-3-trifluoromethyl-N-(2'-hydroxy-2'-methyl-3'-N-(heptafluorobutyramido)propionyl)aniline. (BP-521)

BP-34 (247 mg, 0.80 mmol) under nitrogen with $CH_2Cl_2$ (5 mL), THF (10 mL) and $NEt_3$ (1.1 mL, 0.80 mmol) was cooled to 0° C. and heptafluorobutyryl chloride added (120 μL, 0.80 mmol). After cooling at RT (room temperature) the volatiles were removed. $CH_2Cl_2$ (30 mL) and $H_2O$ (50 mL) were added, the organic layer separated and dried over $MgSO_4$. The product after silica gel ($CHCl_3$/acetone) was isolated as a colorless oil (320 mg, 82% yield).

$^1$H NMR ($CDCl_3$, 500 MHz): δ9.27 (S, Ar—NHC(O); 4.75 (S, C—O$\underline{H}$); 3.82 (m, CC$\underline{H}$, NH).

Example 3

4-nitro-3-trifluoromethyl-4-N-(2'-hydroxy-2'-methyl-3'-pentadecafluorooctyl amido)-propylamide. (BP-562)

To BP-34 (360 mg, 1.17 mmol) was THF (10 mL) and $NEt_3$ (485 μL, 3.5 mmol) were added. The solution was cooled to 0° C. and pentadecyloctanoyl chloride added (295 μL, 1.17 mmol). After reaching RT, the volatiles were removed. After silica gel (CHCl$_3$/acetone), the product was obtained as a pale yellow solid (689 mg, 84% yield).

Mass spectrum (m/z): 704 (MH$^+$); 726 (M+Na$^+$). $^{19}$F NMR (470 MHz, CDCl$^3$): −56.8 ppm, −77.3, −116.3, −118.1, −118.6, −119.1, −119.4, −122.7.

Example 4

4-nitro-3-trifluoromethyl-N-[2'-hydroxyl-2'-methyl-3'-N-(heptafluorobutyl)aminopropionyl]aniline. (BP-626)

BP-33 (50 mg, 0.172 mmol) was dissolved in THF (1 mL) and 2,2,3,3,4,4,4-heptafluorobutyl amine (200 mg, 1 mmol), and heated at 90° C. for 6 hours. After stripping, the solid after silica gel (CH$_2$Cl$_2$/acetone), gave BP-626 as an oil. (61 mg, 72% yield)

mass spectrum (m/z): 590 (MH$^+$), 512 (MNa$^+$)

Example 5

2-thioethylheptafluorobutyramide. (BP-532)

Heptafluorobutyryl chloride (11.9 g, 51 mmol) was added to a solution of 2-(S-triphenylmethylthio) ethylamine (15.58 g, 49 mmol) and NEt$_3$ (5.43 g, 54 mmol) in CH$_2$Cl$_2$ (50 mL) at 0° C. After 2 hours, the reaction was quenched and extracted with H$_2$O (1×20 mL), saturated NaHCO$_3$ (20 mL), and saturated NaCl (20 mL). Solvent were evaporated and the residue crystallized from hexane (150 mL) to yield (23.06 g (91.3%).

mp: 99–104° C.

Trifluoroacetic acid (22.16 g, 194 mmol) was added to a solution of the product (10.02 g, 194 mmol) in CH$_2$Cl$_2$ (20 mL). After 5 minutes, triethylsilane (5.65 g, 49 mmol) was added. Solvent was evaporated and the solid was purified by silica gel chromatography (CH$_2$Cl$_2$) to yield (4.69 g, 88.3%).

Example 6

4-cyano-3-trifluoromethyl-N-[(2'-hydroxy-2'-methyl-3'-S-{{(2"-heptafluorobutyramido)ethyl)thio}propionyl)aniline. (BP-533)

A solution of BP-532 (1.6 g, 5.9 mmol) in THF (5 mL) was added to a suspension of NaH (0.157 g, 6.6 mmol) in THF (2.6 mL) at 0° C. After 30 min, a solution of 4-cyano-3-trifluoromethyl-N-[2,3-epoxy-2-methylpropionyl] aniline (1.58 g, 5.9 mmol) in THF (5 mL) was added at RT. The reaction was quenched with H$_2$O and extracted with Et$_2$O (3×20 mL). Solvent was evaporated and the residue purified by silica gel chromatography (chloroform/acetone) to yield a white, crystalline solid (2.55 g, 79.9% yield).

Example 7

4-cyano-3-trifluoromethyl-N-(2'-hydroxy-2'-methyl-3'-S{2"-heptafluorobutyramido)ethyl)sulphinylipropionyl)aniline. (BP-567+BP-568)

A solution of sodium metaperiodate (0.18 g, 0.86 mmol) in water (10 mL) was added dropwise to a solution of BP-533 (0.39 g, 0.72 mmol) in MeOH (15 mL) at RT. After stirring for 14 hours, the filtered solid was washed with MeOH (15 mL). Volatiles were evaporated in EtOAc (100 mL) and extracted with water (10 mL), 10% aq. sodium sulfite (15 mL) and then saturated NaCl (15 mL). The organic layer was dried over MgSO$_4$ and solvent was evaporated. The residue was purified by silica gel chromatography (50:50 CHCl$_3$/acetone) to yield two diastereomers as white, crystalline solids (0.31 g, 78.0%).

Example 8

4-cyano-3-tri-fluoromethyl-N-[(2'-hydroxy-2'-methyl-3'-S-{(2"-heptafluorobutyramido)ethyl)suffonylipropionyl)aniline. (BP-534)

A solution of MCPBA (0.796 g, 4.6 mmol) in CH$_2$Cl$_2$ (100 mL) was added dropwise to BP-533 (1.09 g, 2.01 mmol) in CH$_2$Cl$_2$ (100 mL). After stirring for 14 hours, the reaction was quenched with 10% aq. sodium sulfite (20 mL), extracted with Na$_2$CO$_3$ (2×15 mL), and brine (15 mL). Solvent was evaporated and the residue purified by silica gel chromatography (CHCl$_3$/acetone) to yield the product as an oil (0.93 g, 79.8%).

Example 9

4-[2",5'-dioxo-3',3'-dimethyl-1'-pyrrolidinyl]-2-trifluoromethyl-benzonitrile. (BP-245)

2,2-dimethyl succinic anhydride (34.41 g, 268 mmol) was placed in a flask and melted at 140° C. under nitrogen. 5-amino-2-trifluoromethyl benzonitrile (25 g, 134 mmol) was added in portions, followed by methanesulfonic acid (500 uL). After two hours, temperature was reduced to 120° C. and EtOAc (200 mL) was added. The solution was washed with NaHCO$_3$ (2×50 mL), then saturated NaCl (50 mL). Drying (MgSO$_4$), filtration, and removal of the solvents left an oil, which was dissolved in toluene (200 mL) at 60° C. After several days, filtration and drying yielded BP-245 (25.7 g, 65%) as colorless crystals.

HPLC purity=99%, melting point: 131–33° C.

Example 10

4-[2',5'-dioxo-3',3',4'-trimethyl-1'-pyrrolidinyl]-2-trifluoromethyl-benzonitrile. (BP420)

BP-245 (10 g, 34 mmol) was dissolved in DMF (40 mL) and THF (20 mL) in a Schlenk flask and cooled to −78° C. under nitrogen. Lithium bis(trimethylsilyl)amide (34 mL, 1 M in THF; 34 mmol) was added over 10 minutes, iodomethane (5.1 g, 35.7 mmol) in THF (20 mL). The reaction was allowed to warm to RT and stirred for 12 hours. The reaction was poured into toluene (400 mL), 1N HCl (200 mL), the layers separated and the toluene layer washed with 50% saturated NaCl (100 mL). Drying (MgSO$_4$), filtration and solvent removal gave a yellow, crystalline solid, which was purified by silica gel (toluene/acetone) and crystallized from toluene (40 mL) to yield a white, crystalline solid. (2.19 g, 21% yield).

Example 11

4-[2'.5'-dioxo-3',3',4',4'-tetramethyl-1'-pyrrolidinyl]-2-trifluoromethyl-benzonitrile. (BP-424)

BP-245 (5.0 g, 16.9 mmol) was dissolved in dry DMF (22 mL) and cooled to −60° C. Lithium bis (trimethylsilyl) amide (33.8 mL 1 M in THF; 33.8 mmol) was added over 10 minutes, followed by iodomethane (5.025 g, 35.4 mmol) in THF (10 mL). After 6 hours at −20° C., mixture was poured into toluene (200 mL) 1 N HCl (100 mL). The layers were separated and the toluene layer washed with saturated NaCl (50 mL). Drying (MgSO$_4$), filtration and solvent removal gave an oil, which was purified on silica gel (toluene/acetone). Yield of BP-424=3.25 g (60%)

melting point: 162.5–164° C.

Example 12

4-[2'-oxo-5'-hydroxy-3',3',4',4'-tetramethyl-1'-pyrrolidinyl]-2-trifluoromethyl-benzonitrile. (BP-511)

BP-424 (100 mg, 0.31 mmol) was dissolved in methanol (2 mL) and 1 N HCl (100 uL). At 15° C., solid sodium borohydride (58 mg, 1.54 mmol) was added over 2 minutes. After 14 hours at RT, methanol was removed, and the product partitioned between EtOAc (20 mL) and 10% NaCl (25 mL). The layers were separated, the organic layer washed with saturated NaCl (25 mL) and dried (MgSO$_4$), and evaporated to give a white solid (109 mg) which was further purified by crystallization from CH$_2$Cl$_2$. (88 mg 87% yield)

Melting point: –195–197° C. Mass spectrum (m/z): 325 (MH+)MW=326.32

Example 13

4-(2'-oxo-5'-heptafluorobutyloxy-3',3',4',4'.-tetramethyl-1'pyrrolidinyl)-2-trifluoromethyl benzonitrile. (BP-569)

BP-511 (100 mg, 0.036 mmol) was suspended in 2,2,3,3,4,4,4-heptafluorobutanol (1 mL) and methanesulfonic acid (100 uL) and was stirred at RT for 6 hours. The solution was poured into 0.1 M K$_2$HPO$_4$ (pH 7.0,15 mL) and EtOAc (25 mL). The organic layer was washed with brine (2×10 mL) and dried (MgSO$_4$). Stripping and silica gel chromatography (CCl$_4$/acetone) gave a white solid (53 mg, 34% yield).

Mass spectrum (m/z): 509 (MH$^+$)

Example 14

4-[3'-(4"-N-t-butoxycarbonyl)-aminobutyl)-4',4'-dimethyl-5'-imino-2'thioxo-1-imidazolidinyl]-2-trifluoromethyl-benzonitrile. (BP-380)

4-cyano-3-trifluoromethyl phenylisothiocyanate (2.3 g, 10 mmol) was dissolved in THF (15 mL), and NEt3 (1.43 mL, 10.3 mmol) then added to crude 2-(1',4'-butylamino-N-tbutoxy-carbonyl)-2-cyanopropane (2.6 g, 10.2 mmol) in THF (10 mL). After 1.5 hours, the volatiles were removed in vacuo. Silica gel column (CHCl$_3$/acetone) gave a yellow solid (3.6 g) 94% pure by HPLC.

$^1$H NMR (500 MHz, CDCl$_3$): δ3.20 (m, 2H, CH$_2$NHC(O)); 3.68 (m, 2H, CH$_2$NC(S)).

Example 15

4-[3'-(4"-aminobutyl)-4', 4'-dimethyl-5'-imino-2'-thioxKo-1-imidazolidinyl-2-trifluoromethyl-benzonitrile. (BP-381)

BP-380 (21.0 g, 44 mmol) was dissolved in MeOH (80 mL). 4 N HCl (40 mL, 160 mmol) and methanol (40 mL) were added. After reflux for 1.5 hr and evaporated. The product was filtered from an EtOH slurry, washed with cold EtOH (50 mL) and dried under vacuum to give a colorless solid (15.8 g, 88.5% yield).

$^1$H NMR (DMSO-d$_6$, 500 MHz): δ3.72 (m, 2H NCH$_2$CH$_2$); 2.82 (m, 2H, CH$_C$CH$_2$NH$_3$); 155 (s, 6H, CCH$_3$).

Example 16

4-[3'-(4"-heptafluorobutyramidobutyl)-4',4'-dimethyl-5'oxo-2'-thioxo-1-imidazolidinyl]-2-trifluoromethyl-benzonitrile. (BP-443)

BP-381 (15.8 g, 37.6 mmol) was placed in a flask with CH$_2$Cl$_2$ (200 mL) and NEt$_3$ (23 mL, 165 mmol). Heptafluorobutyryl chloride was added (6.2 mL, 41.3 mmol). After stirring for 6 hours at RT and everything followed by silica gel (CHCl$_3$/acetone). An oil (8.9 g) resulted (41% Yield).

$^{19}$F NMRCDCl$_3$); –58.5 ppm (ArCF$_3$); –77.1 (CF$_2$CF$_3$); –117.2 (C(O)CF$_3$); –123.4 (CF$_2$CF$_2$CF$_3$). $^{13}$C NMR (CDCl$_3$ 127 MHz): 157.8 ppm 175.13, 178.55.

Example 17

4-[3'-((4"-heptaflurobutylamidoethyl)butyl)-4',4'-dimethyl-5'-imino-2'-thioxo-1-imidazolidinyl]-2-trifluoromethyl benzonitrile. (BP-444)

BP-138 (340 mg, 0.95 mmol; acc. to example 7) was dissolved in CH$_2$Cl$_2$ (5 mL) and NEt$_3$ (0.397 mL, 2.85 mmol). Heptafluorobutyryl chloride was added (0.142 mL, 0.95 mmol). After 30 minutes at RT, the volatiles were removed. Silica gel (CHCl$_3$/acetone) gave a colorless solid (280 mg) (5% Yield).

$^{19}$F NMR (470 MHz, CDCl$_3$): –58.6 ppm, –77.0, –117.0, –123.3.

Example 18

N-(4-cyano-3-trifluoromethyl-phenyl)-N'-heptafluorobutyl) thiourea. (BP-628)

4-cyano-3-trifluoromethyl phenylisothiocyanate (2.28 g, 10 mmol) was dissolved in THF (15 mL), and cooled to 5° C. 2,2,3,3,4,4-heptafluorobutyl amine (209 mg, 10.5 mmol) was added after stirring for 1 hour, with EtOAc (60 mL) and 1 N HCl (25 mL) were added. The organic layer was washed with saturated NaCl (15 mL) and dried (MgSO$_4$). Silica gel chromatography (CH$_2$Cl$_2$/acetone), gave a white solid (90% yield).

Example 19

4-nitro-3-trifluoromethyl-N-[2'-hydroxy-2'-methyl-3'-{N'-(methyl)-N'-(3"-phenyl-3"-(oxy-p-trifluoromethyl phenyl))propyl}amino]aniline. (BP-657)

BP-33 (77 mg, 0.264 mmol) and fluoxetine (68 mg, 0.22 mmol) were dissolved in p-dioxane (3 mL) and the solution heated for 6 hours at 95° C. The solvent was removed and the product purified on silica gel (CH$_2$Cl$_2$ /MeOH/NEt$_3$). Yield=64 mg (48% Yield).

Example 20

2-hydroxy-3-((2-hydroxy-2-(N-(4-nitro-3-(trifluoromethyl)phenyl) carbamoyl)propyl) amino)-2-methyl-N-(4-nitro-3-(trifluoromethyl)phenyl) propionamide. (BP-673)

BP-33 (1.0 g, 34 mmol) was dissolved in methanol (40 mL). NH$_4$OH (30%, 4 mL) was added and the reaction stirred at room temperature for 24 hours. The volatiles were removed and the crude solid chased with methanol (2×10 mL). The product was collected as a precipitate from methylene chloride and further purified using column chromatography (CH$_2$Cl$_2$/MeOH gradient) to give a yellow solid. Yield of BP-673=490 mg (48%).

Mass Spectrum (m/z): MH$^+$598.

Example 21

2-hydroxy-3-((2-(2-(2-hydroxy-2-(N-(4-nitro-3-(trifluoromethyl)phenyl)carbamoyl)propyl)amino) ethoxy) ethoxy)ethyl)amino)-2-methyl-N-(4-nitro-3 (trifluoromethyl) phenyl)propanamide. (BP-676).

BP-33 (500 mg, 1.72 mmol) was placed in flask with stir bar. Dioxane was added. In a separate flask, dissolved diamine (Hunstman XTJ-504) (127 mg, 0.86 mmol) in Dioxane (4 mL). This was added to the former and the resulting solution was stirred and heated at 90° C. for 5 hours. The oil bath was removed and the reaction stirred for 9 hours at room temperature. The volatiles were removed and chloroform added (10 mL), to give a colorless precipitate, which was collected and dried to give the product as a colorless solid. Yield of BP-676=290 mg (46%).

Mass Spectrum (m/z): MH$^+$=729

Example 22

N-(4-chlorophenyl)-3-((2-(N-(4-chlorophenyl) carbamoyl)-2-hydroxypropyl)amino)-2-hydroxy-2-methylpropanamide. (BP-708)

BP-706 (3.0 g, 14.2 mmol) was dissolved in CH$_3$OH in flask and stir bar. NH$_4$OH (12 mL) was added turning solution into yellow liquid. After stirring two days, the volatiles were removed and the crude product chased with MeOH (2×120 mL). The product was purified using column chromatography (CH$_2$Cl$_2$: MeOH gradient) and isolated to produce white crystals. Yield of BP-708=2.56 g (41%).

Mass Spectrum (m/z): MH$^+$=440 mp. 76–78° C.

Example 23

3-((((4-bromophenyl)amino)thioxomethyl)amino)-2-hydroxy-2-methyl-N-(4-nitro-3-(trifluoromethyl) phenyl)propanamide. (BP-668)

BP-34 (2.0 g, 6.5 mmol) was dissolved in anhydrous THF (30 mL) under N$_2$(g). NEt$_3$ was added (100 μL). In a separate flask under N$_2$(g), 4-bromophenylisothiocyamate was similarly added to the former mixture. After stirring for 1 hour, the volatiles were removed and the crude product purified via silica gel column chromatography (CHCl$_3$/acetone gradient) to give the product as a yellow solid (m.p. 192–195° C.) in 67% yield.

Mass Spectrum (m/z): MH$_+$=521, 523

Example 24

3-(((((cyclohexylmethyl)amino)thioxomethyl)amino)-2-hydroxy-2-methyl-N(4-nitro-3-(trifluoromethyl) phenyl)propanamide. (BP-743)

BP-34 (2.0 g, 6.5 mmol) was dissolved in anhydrous THF (30 mL) under N$_2$(g). NEt$_3$ was added (2.7 mL) and then followed by cyclohexylmethylisothiocyanate (1.0 g, 6.4 mmol). After stirring for 3 hours, the volatiles were removed and product purified via silica gel column chromatography (CH$_2$Cl$_2$: acetone gradient) to give a yellow solid (m.p. 77–81° C.) in 84% yield.

Mass Spectrum (m/z): MH$^+$=463; MNa$^+$=485.

Example 25

4-[2',5'-dioxo-3',3',4'-trimethyl-4'-propynyl-1'-pyrrolidinyl]-2-trifluoromethyl-benzonitrile. (BP-535)

BP-420 (1.71 g, 5.5 mmol) was placed in a flask. After cooling to −50° C., lithium bis(trimethylsilyl)amide (5.55 mL, 1 M in THF; 5.55 mmol) was added, followed by propargyl bromide (0.69 g, 58 mmol). The reaction was held at 0° C. overnight after which it was poured into 1 N HCl (30 mL) and extracted with EtOAc. The organic layer was washed with 50% saturated NaCl (100 mL). Drying (MgSO$_4$), filtration and solvent removal gave a solid, which was purified on silica gel (toluene/acetone). The product was re-crystallized from toluene (1.05 g, 55% yield).

Example 26

2-(trifluoromethyl)-4-(3,3,4-trimethyl-2,5-dioxo-4-(6,7,7-trifluorohept-6-en-2-ynyl)cyclopentyl) benzenecarbonitrile. (BP-751)

BP-535 (120 mg, 0.34 mmol) is dissolved in anhydrous THF (10 mL) and the solution cooled to −78° C. KN(SiMe$_3$)$_2$ (344 μL, 1 M in toluene) is added, followed by BrCH$_2$CH$_2$CF=CF$_2$ (65 mg, 0.34 mmol). The solution is allowed to warm to RT, is quenched with 1 N HCl and extracted with EtOAc. The layers are separated and the organic layer dried (MgSO$_4$), filtered and concentrated to give the crude product, which is purified via column chromatography to give the product as a colorless solid.

Example 27

4-cyano-3-trifluoromethyl-N-(2'-hydroxy-2'-methyl-3'-N-(heptafluorobutyramido)propionyl) aniline (BP-713)

BP-646 (the cyano analog of BP-34)(1.121 g, 3.89 mmol) was dissolved in dry CH$_2$Cl$_2$ and NEt$_3$ (1.6 mL) was added. Heptafluorobutyryl chloride was added (558 μl, 4.28 mmol). After 3 hours, volatiles were removed and the product purified by silica gel chromatography (CH$_2$Cl$_2$/acetone) to give a colorless solid (1.03 g, 55% yield)

Mass spectrum (m/z): 482(MH$^+$). Melting point 142–144EC

Example 28

N-(3-trifluoromethyl-4-cyanophenyl), N'-propyl thiourea (BP-735)

4-Cyano-3-trifluoromethylphenylisothiocyanate (1 g., 4.39 mmol) was dissolved in anhydrous THF (30 mL) and cooled to OEC. n-Propylamine was added slowly and the ice bath removed. After stirring at RT for 16 hours, volatiles were removed and the product was crystallized from toluene to give off-white plates (1.02 g, 77% yield).

Example 29

2-hydroxy-3-(((4'-iodophenyl)amino) carbonylamino)-2-methyl-N-(4"-nitro-3"-trifluoromethyl)phenyl)propanamide (BP-754)

BP-34 (2.35 g., 7.66 mmol) was dissolved in anhydrous THF (25 mmol). In a separate flask, p-iodophenylisocyanate (2.0 g., 8.16 mmol) was dissolved in anhydrous THF (10 mL). NEt$_3$ (3.2 mL) was added to the first solution, followed by addition of the isocyanate solution. After 2 hours, the volatiles were removed and the crude product washed with $CH_2Cl_2$ (2×50 mL) and the a resulting product collected as a pale yellow solid (4.0 g., 95% yield).

Example 30

4-[3'-trans-(2"-propenyl-3"-iodo)-4',4'-dimethyl-5'-oxo-2'-thioxo-1-imidazolidinyl]-2-trifluoromethylbenzonitrile (BP-305): 4-[3'-cis-(2"-propenyl-3"iodo)-4',4'-dimethyl-5'-oxo-2'-thiooxo-1'-imnidazolidinyl]-2-trifluoromethylbenzonitrile (BP-305)

BP-199 (4-[4',4'-dimethyl-3-propargyl-5'-oxo-2'-thioxo-1-imidazolidinyl]-2-trifluoromethylbenzonitrile; see WO97/00071) was dissolved in dry toluene (100 mL) under $N_2$. $Bu_3SnH$ (1.12 mL) and AIBN (68.5 mg) were added and the reaction mixture heated to reflux. After stirring for 3 hours at reflux, the reaction was allowed to cool to Rt and the volatiles removed under vacuum. The crude product was purified by column chromatography ($SiO_2$, eluent $CHCl_3$) isolated as a pale oil (1.67 g). Purity 95.3% HPLC.

BP-237 (80:20 E/Z isomers, 370 mg) was dissolved in $CHCl_3$ (5 mL) and cooled to OEC. In a separate flask, $I_2$ (146 mg) was dissolved in $CHCl_3$ (15 mL) and added to the solution of BP-237. After 2 hours at RT, the volatiles were removed and the product mixture purified using silica chromatography (gradient $CHCl_3$/acetone). BP-305 (trans isomer) was isolated as a white crystalline solid 200 mg, m.p. 137–139EC. Purity was 96.4% (contaminated with 1.2% of BP-307 (HPLC)). Pure BP-307 was obtained by further use of column chromatography (70 mg, m.p. 146-7EC, purity 99.2%:HPLC)

Example 31

4-cyano-3-trifluoromethyl-N-[2'-hydroxy-2'-methyl-3'-(propargyloxvpropionyl]aniline (BP-632)

To a solution of propargyl alcohol (2.59 mL, 44.5 mmole) cooled to −78EC was added dropwise a solution of methyl lithium in diethyl ether (27.8 mL, 1.6M). After 30 min a solution of 4-cyano-3-trifluoromethyl-N-[2,3-epoxy-2-methylpropionyl]aniline (4.0 g, 14.8 mmole; prepared according to the general method in EP 0 100 172) in THF (40 mL) was added. The solution was allowed to reach RT, stirred 20 hours and the volatiles removed. The residue was partitioned between THF/sat. aq. NaCl (50 mL/50 mL), the organic layer concentrated under reduced pressure to an oil and purified by silica chromatography ($CHCl_3$/acetone) to yield 4.27 g (88%) BP-632.

Example 32

4-cyano-3-trifluoromethyl-N-[2'-hydroxy-2'-methyl-3'-[3"-(125I)iodo-trans-2"-propenyloxy]propionyl aniline (BP-636): 4-cyano-3-trifuoromethyl-N-[2'-hydroxy-2'-methyl-3'-[3"-(125I)iodo-cis-2"-propenyloxy]propionyl aniline (BP-637); 4-cyano-3-trifluoromethyl-N-[2'-hydroxy-2'-methyl-3'-[gem-di-3"-(125I)iodo-2"-propenyloxy]propionyl aniline (BP-638)

A. 4-cyano-3-trifluoromethyl-N-[2'-hydroxy-2'-methyl-3'-[3"-tributylstannyl-trans-2"-propenyloxy]propionyl aniline (BP-633): 4-cyano-3-trifluoromethyl-N-[2'-hydroxy-2'-methyl-3'-]3"-tributylstannyl-cis-2"-propenyloxy]propionyl aniline (BP-634): 4-cyano-3-trifluoromenthyl-N-[2'-hydroxy-2'-methyl-3'-[gem-di-tributylstannyl-2"-propenyloxy]propionyl aniline (BP-635)

To a solution of BP-632 (2.60 g, 8.0 mmole) in toluene (30 mL) was added BuSnH (3.21 mL, 12.0 mmole) and AIBN (1.39 g, 12.0 mmole). The solution was refluxed for 20 hours, the volatiles removed and the crude product purified on silica chromatography ($CHCl_3$/acetone) to yield 4.07 g (89%) of an 8:1:1 mixture of trans, cis and gem isomers (BP-633, -634, -635)

B. The mixture prepared above is dissolved in a small amount of DMF. Radioiodination is accomplished using $Na[^{123}]I$, $Na[^{125}]I$ or $Na[^{131}]I$ by known methods. (See Hunter and Greenwood, Nature (1962) 194:495-6)

Example 33

4-cyano-3-trifluoromethyl-N-[2'-hydroxy-2'-methyl-3'-[3"-(125I)iodo-trans-2"-propenylthio]propionyl aniline (BP-552): 4-cyano-3-trifluoromethyl-N-[2'-hydroxy-2'-methyl-3'-[3"-(125I)iodo-cis-2"-propenylthio]propionyl aniline (BP-553); 4-cyano-3-trifluoromethyl-N-[2'-hydroxy-2'-methyl-3'-]gem-di-3"-(125I)iodo-2"-propenylthio]propionyl -aniline (BP-554)

A. A solution of propargylthiol (100 mL, 0.13M in THF/$CH_2Cl_2$; prepared according to Castro, J. et al., Synthesis 1977, 518) was added to a suspension of NaH (0.52 g, 13.0 mmole, 60% in oil) in THF (25 mL) at −78° C. and stirred for 1 hour. To this cold solution was added a solution of 4cyano-3-trifluoromethyl-N-[2,3-epoxy-2-methylpropionyl] aniline (3.51 g, 13.0 mmole; prepared according to EP 0 100 172 general method) in THF (20 mL) and stirred 1 hour at −78° C. The solution was allowed to reach RT, stirred 1 hour and the volatiles removed. The residue was partitioned between $CHCl_3/H_2O$ (200 mL/200 mL), the organic layer concentrated to an oil under reduced pressure and purified by silica chromatography ($CH_2Cl_2$) to yield 1.13 g (25%) BP-548

B. 4-cyano-3-trifluoromethyl-N-[2'-hydroxy-2'-methyl-3'-[3"-tributylstannyl-trans-2"-propenylthio]propionyl]aniline (BP-549): 4-cyano-3-trifluoromethyl-N-[2'-hydroxy-2'-methyl-3'-[3"-tributylstannyl-cis-2"-propenylthio]propionyl] aniline (BP-550); 4-cyano-3-trifluoromethyl-N-[2'-hydroxy-2'-methyl-3'-[gem-2"-di-3"-tributylstannyl-2"-propenylthio]propionyl]aniline (BP-551)

BP-548 (1.03 g, 30 mmole) was dissolved in 1,4-dioxane (15 mL) and toluene (30 mL). $Bu_3SnH$ (1.21 mL, 4.5 mmole) and AIBN (0.52 g, 4.5 mmole) were added and the reaction mixture heated to reflux for 12 hours. The volatiles were removed and the crude product was purified on silica chromatography ($CHCl_3$) to yield 0.78 g (44%) of a 5:3:2 mixture of the gem, cis and trans isomers. (BP-551, -550, and -549, respectively).

C. The mixture of BP-549, -550 and -551 prepared above is dissolved in a small amount of DMF. Radioiodination is accomplished using $Na[^{123}]I$, $Na[^{125}]I$ or $Na[^{131}]I$ by known methods. (See Hunter and Greenwood, Nature (1962) 194:495–6).

Compounds were tested for stability in human serum at 38° C. They were dissolved in isopropanol/$H_2O$ (95:5), mixed with human serum to a concentration of 0.5 mg/mL, and incubated at 38° C. Serum aliquots were extracted with ethyl acetate and analyzed by HPLC. In an accelerated stability study of the compounds BP-521, BP-668 and BP-673, formulated in isopropanol/$H_2O$ (95:5) and incubated at 50° C., no change was observed via HPLC up to six days.

TABLE 1

Percent of the intact compound remaining in
human serum at 38° C. after incubation.

| Compound | 6 h | 24 h | 48 h | 6 d |
|---|---|---|---|---|
| BP-521 | 97.5 | 90.0 | 84.0 | 60.0 |
| BP-668 | — | 100 | 100 | 100 |
| BP-673 | — | 100 | 100 | 100 |

It can be seen that the compound containing aliphatic perfluorocarbon has a limited stability resulting from hydrolysis of the perfluoroamide, leaving the free amine, BP-34 (Example 1) and the perfluorocarbon moiety. Compounds BP-673 (a dimeric species) and BP-668 have nevertheless proved stable.

Compounds which were found sufficiently stable were dissolved in EtOH/DMSO and incubated with human prostate cancer cells LNCaP, which contain AR with a minor mutation. After 72 hours, an XXT assay (Scudievo, et al., Cancer Research, 48:4827 (1988)) indicating cell viability was carried out. Table 2 shows the lowest drug concentrations needed to abolish 50% of the cellular viability.

TABLE 2

Effect on cell viability

| Compound: | Molar Concentration: |
|---|---|
| Bicalutamide | 7.0 H 10−5 |
| Hydroxyflutamide | 5.0 H 10−5 |
| BP-34 | <1 H 10−4 |
| BP-443 | 5.5 H 10−6 |
| BP-463 | 5.5 H 10−5 |
| BP-483 | 6.25 H 10−6 |
| BP-521 | 5.6 H 10−6 |
| BP-546 | 4 H 10−6 |
| BP-668 | 1.5 H 10−5 |
| BP-673 | 2.7 H 10−5 |
| BP-676 | 1.4 H 10−5 |
| BP-713 | 1 H 10−5 |

The interaction of the compounds with AR was studied by incubation with LNCaP cells, subsequent cell lysis and the standard Western Blot assay. Table 3 shows percent of remaining AR contained in the lysate following incubation of the cells with test compounds for 48 hours.

TABLE 3

Percent of the androgen receptor remaining in human prostate cancer
cells, LNCaP, by Western Blot.

| Compound: | @ 3μ Molar conc.: | @ 10μ Molar conc.: |
|---|---|---|
| BP-34 | 97 | 98 |
| BP-52 | 38 | 0 |
| BP-668 | 73 | 0 |
| BP-673 | 74 | 3 |
| BP-676 | 64 | 20 |
| BP-713 | 50 | 3 |
| BP-735 | 45 | 1 |
| BP-754 | 28 | 14 |
| Bicalutamide | 97 | 89 |
| Hydroxyflutamide | 98 | 94 |

It can be seen that not all compounds which showed strong inhibition of LNCaP cells, by XXT assay, were also correspondingly active in suppressing the AR. While the control antiandrogens, i.e. hydroxyflutamide and bicalutamide, have not shown any significant effect on the AR, important suppression was found at 3 μM concentration with compounds BP-521, BP-673, BP-668, BP-713 and BP-735. These compounds practically eliminated the AR at 10 μM concentration.

The free amine, BP-34, a product of the composition of BP-521, had no effect on the AR, nor on the LNCaP cells.

BP-521 bioavailability results are shown in Table 4.

TABLE 4

Bioavailability of BP-521

| Species | Applic./dose in mg/kg bw | μg/ml blood at hrs.: | | | | | | Cumulative mg/total blood volume | |
|---|---|---|---|---|---|---|---|---|---|
| | | 0.5 | 1.0 | 1.5 | 2.5 | 7.0 | 24 | and % dose | |
| Rabbit ~3 kg | oral, 100 | 1.5 | 1.7 | 2.6 | 1.5 | 1.0 | 1.0 | 3.0 μg | 1.50% |
| Rabbit ~3 kg | i.p., 150 | 1.9 | 3.2 | 1.9 | 1.5 | 3.0 | 2.2 | 11.6 μg | 2.8% |
| Rabbit ~3 kg | skin 20 cm² 100 mg/d, 10 d | 0 | 0 | 0 | 0 | 0 | 0 | 0 | 0 |
| Rat ~140 g | i.m., 75 | 0.7 | 4.7 | 2.2 | — | — | 1.0 | 2.1 μg | 2.9% |

It can be seen that only a fraction of the dose is systemically available upon oral, i.p. or i.m. application, that the peak serum levels in the oral test was 0.0052% of the injected dose, as compared to the 0.03% reported for bicalutamide (Cockshott I. D., et al. *Eur Urol.* 1990, Vol 18, Suppl. 3: 10–17). The bioavailability of BP-521 from the subcutaneous, muscle and intraperitoneal spaces was also low.

When intact rats were given 10 times subcutaneously 100 mg/kg of BP-521, the average weight of their prostate and seminal vesicles was reduced by about 46%. On the other hand, 0.1 mg/kg dose of BP-521 or BP-668 in castrated rats supplemented with testosterone propionate did not reduce the secondary sex organs' weight, while 0.5 mg/kg of bicalutamide did, by about 20%. (The dose of 0.1 mg/kg approximates the expected topical daily dose for humans).

Topical absorption was studied in rabbits who were treated 2×daily with 0.5 mL of a 10% solution of BP-521 in 50/50 PEG 400/EtOH over a shaved skin area of 20 cm² No absorption was found by HPLC with standard calibrated sensitivity of detection of 5 nanogramns.

Systemic toxicity was orientationally evaluated by i.p. injection every 2nd day in mice. BP-521, 200 mg/kg bw was given 5 times, without mortality or morbidity, while morbidity but no mortality was seen at 350 mg/kg bw. For BP-34, the corresponding values were 150 mg/kg bw and 300 mg/kg bw.

In an orientational test on three male volunteers, 1% solution of BP-521 in ethanol, 0.5 mL applied twice daily on the affected scalp, effectively arrested incipient androgenic alopecia of the forehead line and after 8 weeks, induced copious growth of vellum hair.

It can be concluded that BP-521, due to the low systemic toxicity and lack of cutaneous absorption and the generally low bioavailability is suitable for treatment of skin disorders where slow biodegradability is an advantage: the resulting free amine, BP-34, has no antiandrogenic activity, and the other decomposition product, perfluorobutyric acid, was shown to have low toxicity (Takagi A., et al. *Cancer Letters.* 1991, 57: 55–60).

Test compounds containing non-radioactive iodine (BP-554, -636 and -305 were shown to interact with AR as compared to controls. These compounds were formulated using a standard medium comprising ethanol, DMSO, Tween and dextrose in water and were injected intravenously into 300 g male rats. After 4 hours the rats were sacrificed and the amount of the test element determined in various organs and blood relative to the prostate levels. There was a substantial accumulation in the prostate vis-a-vis the other tissues which were analyzed. As described in U.S. Pat. No. 5,656,651, the subject compounds can be used for whole body scanning to depict prostate cancer and metastases.

Example 34

4-nitro-3-trifluoromethyl-N-(2'-hydroxy-2'-methyl-3'-N-(trifluoromethylamido)propionyl) aniline (BP-766)

Figure 1:
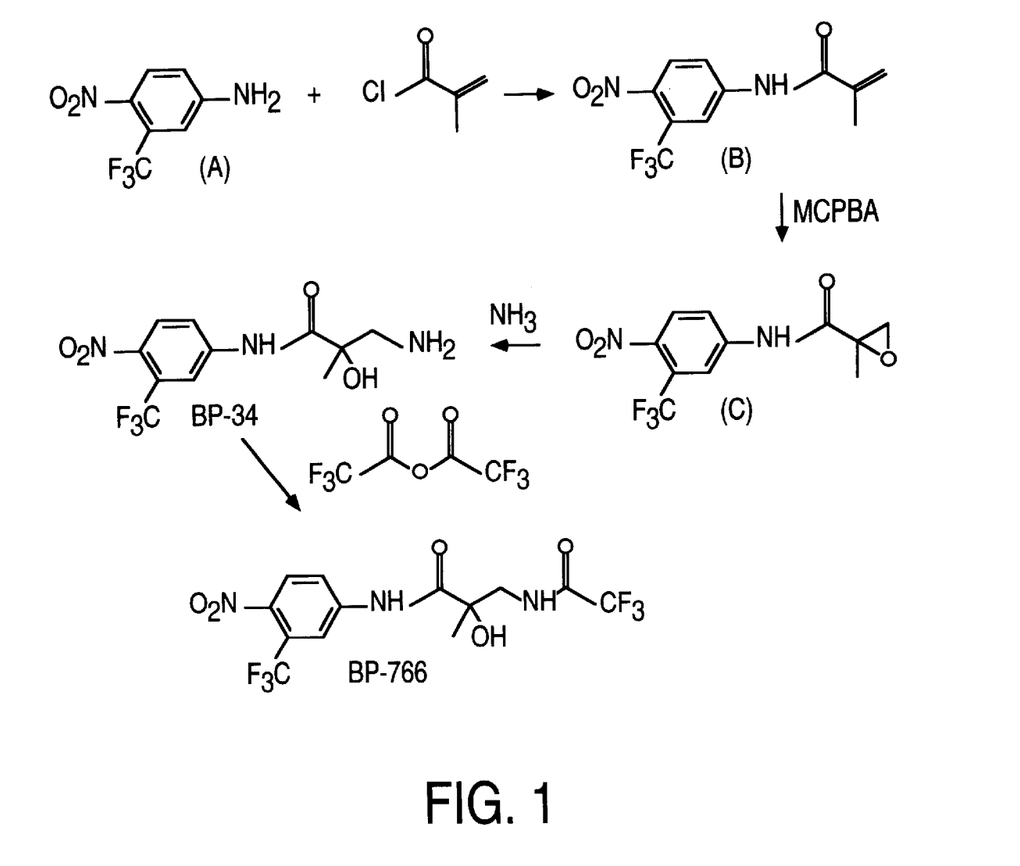
FIG. 1. BP-766 Synthesis. For A, B, C see EP 100172.

Under $N_2$BP-34 (500 g, 1.63 mol), ethyl acetate (2.0 L) and triethylamine (295 mL. 2.12 mol) were stirred at 5° C. Trifluoroacetic anhydride (299 mL. 2.12 mol) was added, stirred for 30 min at RT. then washed in 1N hydrochloric acid (1.0 L), saturated aqueous bicarbonate (2×2.0 L) and brine (1.0 L). After treatment with $MgSO_4$, the solvent was evaporated, and the residue purified (see FIG. 1).

$^1$H NMR (DMSO-$d_6$, 500 MHz): $\delta$10.56 ($s_1$Ar0NHC(O)); $\delta$9.31 t, NHC(O)CF$_3$). $^{19}$F NMR (DMSO-$d_6$, 470 MHZ): $\delta$-58.4 ($s_1$ArCF3); $\delta$-73.4 ($s_1$C(O)CF$_3$). Mass spec (m/z): 426 (MNa$^+$).

Shelf-Stability of Formulated BP-766

An accelerated stability study, to simulating shelf storage, was conducted by incubating formulated solutions of BP-766 (see FIG. 2) at 55° C. and comparing them to storage at room temperature. BP-766 in 97% isopropanol or ethanol:water (60:40), incubated at 55° C. or room temperature showed a small change, by HPLC, for up to six days. (Table 5). This, on average, equates to one year at room temperature. Next BP-766 was incubated at 50° C. for 8 weeks in anhydrous isopropanol to see if it would be reasonably stable over even longer periods of time. Table 6 shows the stability of BP-766 in anhydrous isopropanol. Eight weeks at 50° C. is equivalent to five years at room temperature (20° C.) with no significant decomposition, using the average activity coefficient of a pharmaceutical (Connors, Kenneth A.; Amidon, Gordon L.; Stella, Valentino J. *Chemical Stability of Pharmaceuticals—A Handbook for Pharmacists*. 2d Ed., copyright 1986, John Wiley & Sons, Inc.).

TABLE 5

Accelerated Shelf/Stability of Formulated BP-766

| Time (hours) | % BP-766 Isopropanol (3-5% water) (55° C.) | % BP-766 60/40 EtOH/H$_2$O (RT) | % BP-766 60/40 EtOH/H$_2$O (55° C.) |
|---|---|---|---|
| 0 | 100 | 100 | 100 |
| 6 | 99.6 | — | — |
| 24 | 99.1 | 99.9 | 98.1 |
| 48 | — | 99.69 | 98.2 |
| 144 | 98.7 | — | — |

TABLE 6

Accelerated Shelf/Stability of Formulated in Anhydrous Isopropanol

| | Time (weeks) | | | | | | | | |
|---|---|---|---|---|---|---|---|---|---|
| | 0 | 1 | 2 | 3 | 4 | 5 | 6 | 7 | 8 |
| % BP-766 | 100 | 99.6 | 99.4 | 99.3 | 99.2 | 98.9 | 98.8 | 98.3 | 98.4 |

Effects of BP-766 on the Androgen Receptor

The interaction of the BP-766 with AR was studied by incubation with LNCaP cells, known to contain human AR subsequent cell lysis and the standard Western Blot assay to identify and quantify the AR protein. Table 7 below, shows percent of remaining AR contained in the lysate following 16, 24 and 48 hour incubation of the cells with BP-766 versus its byproduct of biodegradation BP-34. Also, as a control, two standard systemic antiandrogens, bicalutamide and hydroxyflutamide were used.

TABLE 7

Percent Androgen Receptor Remaining in LNCaP Cells by Western Blot

| Compound: | @ 3$\mu$ Molar conc: | @ 10$\mu$ Molar conc: |
|---|---|---|
| B-766 | 42, 52 | 9, 9 |
| ran in duplicate | (average = 47) | (average = 9) |
| 16 hour incubation | | |
| BP-766 | 39, 62 | 6, 8.5 |
| 24 hour incubation | (average = 51) | (average = 7.3) |
| BP-766 | 51, 67 | 0.1, 8 |
| 48 hour incubation | (average = 59) | (average = 4.1) |
| BP-34 | 97 | 98 |
| Bicalutamide | 98 | 89 |
| Hydroxyflutamide | 98 | 94 |

The systemic antiandrogens, hydroxyflutamide and bicalutamide, have not shown any significant suppression of the AR, however, important suppression was found at 3 and 10 $\mu$M concentrations of BP-766. BP-766 practically eliminated the AR to 10 $\mu$M concentration.

BP-34 had no effect on the AR.

Cutaneous Absorption and Irritation Studies in Rabbits

BP-766 was applied topically twice daily to simulate the intended human application (0.6 mg/kg-day), on the two separate areas of a closely shaved skin of four rabbits for ten days. Serum samples were collected at 2, 5 and 21 hours after the first application, and once every other day, thereafter. Serum samples were processed and analyzed by HPLC. Using spiked and blank serum samples and a linearity determination, we determined the limits of detection of BP-766 and/or BP-34 as approximately 10 ng/ml. No. BP-766 or BP-34 were found in any of the samples. The cutaneous absorption in rabbits is known to be about 5 to 6 times greater than in humans (Marzulli, F. N. and Maibach, HI *Dermatotoxicology*, 5$^{th}$ Ed., Taylor & Frasier, Washington, D.C. 1966) so that even when we consider the detection limitation of this method, only traces, at worst, could be expected in the human serum.

The rabbits were also observed daily for signs of cutaneous irritation. No signs of irritation were noted over the entire course of the experiment.

Biodegradability of BP-766 in Human Serum

Figure 2:
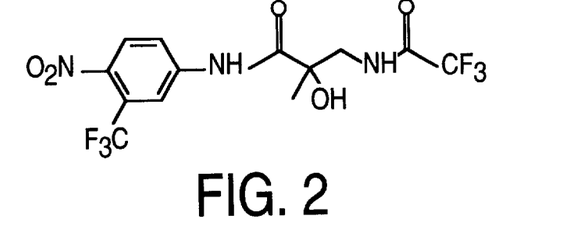
FIG. 2. The structure of BP-766.
Figure 3:
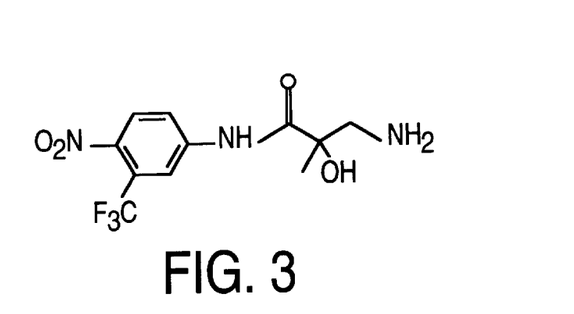
FIG. 3. The structure of BP-34.
Figure 4:
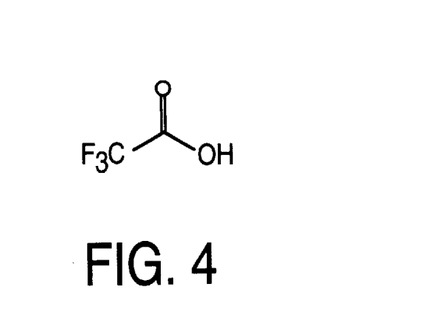
FIG. 4. The structure of trifluoroacetic acid.
Figure 5:
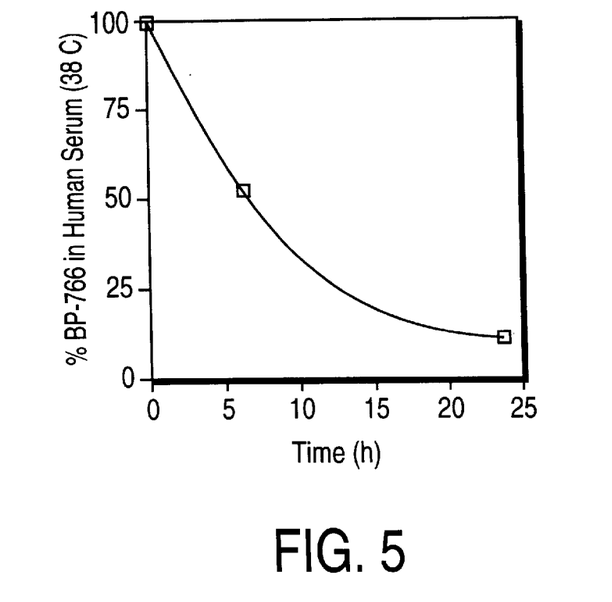
FIG. 5. Biodegradability of BP-766 in serum.

BP-766 was tested for biodegradability in human serum at 38° C. at a concentration of 0.5 mg/mL, and incubated at 38° C. The percent of intact compound found by HPLC over time in serum, incubated at body temperature, is reported in Table 8 and depicted in FIG. 5. Obviously, should for any unexpected reason the topical BP-766 be resorbed, it would be desirable that it break down to rapidly excretable non-toxic components,. The only products of biodegradation of BP-766 are BP-34, and trifluoroacetic acid, which appear to have low toxicity. Thus, trifluoroacetic acid, showed no toxicity when fed to mice. (Permadi, H.; Lundgren, B.; Andersson, K.; Sundberg, C.; DePierre, J. W. Effects of perfluoro fatty acids on peroxisome proliferation and mitochondrial size in mouse liver: dose and time factors and effect of chain length. *Xenobiotica,* 91993) Vol. 23, No. 7, pp.761–70). The chemical structures of BP-766, BP-34, and trifluoroacetic acid are depicted in FIGS. 2–4.

TABLE 8

Biodegradability of BP-766 in Human Serum; Percent Remaining BP-766 Over Time

| Time (hours) | % BP-766 human serum (38 C) |
|---|---|
| 0 | 100 |
| 6 | 54.3 |
| 24 | 10.9 |
| 48 | Traces |

Systemic Toxicity of BP-766

The systemic toxicity of BP-766 was orientationally evaluated by multiple i.p. injections in mice. BP-766 was injected daily for seven days each time at a dose of 300 to 500 mg/kg bw. The $LD_{50}$ (daily dose for seven days that resulted in 50% mortality) of BP-766 was estimated at 450 mg/kg bw. The maximum tolerated dose should thus be approximately 300 mg/kg. For BP-34, i.p. injections of 100–300 mg/kg produce no mortalities in mice. Morbidity, but not mortality, was observed at 300 mg/kg. Therefore, the maximum tolerated dose of BP-34 should be approximately 250 mg/kg.

Acute Oral Toxicity in Mice and Rats

The acute oral toxicity of BP-766 was determined in NMRI mice and Wistar rats. The $LD_{50}$ was calculated by probit analysis, with 5 mice or rats at each dose level (1500, 2000 and 2500 mg/kg) tested.

The $LD_{50}$ of BP-766 in male and female NMRI mice was calculated as 2871.7 mg/kg and 2232.0 mg/kg respectively. The $LD_{50}$ of BP-766 in male and female Wistar rats could not be determined since only one male rat died (at the 1500 mg/kg dose), and none of the female rats died. Therefore, the $LD_{50}$ of BP-766 in rats is much greater than the highest dose tested, i.e. 2500 mg/kg body weight.

Pilot Observations of Efficacy of BP-766 in the Treatment of Alopecia

BP-766 has been tested in six volunteers with androgenic effluvium and alopecia. In six (4 male, 2 female) volunteers BP-766 was applied directly on the skin (behind the hair-thinning line) as a 2% solution in anhydrous isopropanol, 1 ml, twice daily (0.6 mg/kg) for a period of 8 weeks; no dermal irritation was seen in any of the volunteers. Preliminary results have shown that BP-766 arrested the effluvium of the frontal hairline in all six volunteers after 2 weeks. After 4 months use, by two volunteers, an evident regrowth was observed.

CONCLUSIONS

It can be concluded that BP-766, due to the lack of topical toxicity, lack of systemic absorption, and biodegradability, is suitable for the treatment of skin disorders requiring anti-androgens.

It is evident from the above results that compounds are provided which are effective with indications associated with the androgen receptor, such as androgen dependent tumors, and skin androgen mediated disorders, such as acne, hirsutism and androgenetic alopecia. In addition to having cytotoxic and cytostatic activity, some of the compounds demonstrate androgen receptor suppression. For topical treatment, compounds are provided which have low resorption.

Although the foregoing invention has been described in some detail by way of illustration and example for purposes of clarity of understanding, it will be obvious that certain changes and modifications may be practiced within the scope of the appended claims. All references cited herein are incorporated herein by reference, as if set forth in their entirety.

What is claimed is:

1. A compound of the formula:

wherein:

X is nitro, cyano or halogen;

V is $CF_3$, halogen or H;

W is OH when T is H and is methyl when T and $T^1$ are taken together to form a C=Z bridge;

U is N when T and $T^1$ are taken together to form a C=Z bridge or is taken together with $T^1$ to form a bond or O or N;

Q is a chalcogen;

n is 1 or 2 and d is 0 or 1;

when d is 0, T and $T^1$ are hydrogen;

when d is 1, then:

when n is 1, Y is a bond or linking group of from 1 to 10 carbon atoms and from 0 to 6 heteroatoms in the chain, where the heteroatoms are N, O, or S;

Z, when other than taken together with Y, is an aliphatic group of from 1 to 6 carbon atoms, a polyfluoroacylamido group of from 2 to 8, carbon atoms and having at least 2 fluorines and not more than 2m−1 fluorines, wherein m is the number of carbon atoms, or haloanilino, where halo is of atomic number 9 to 80; and when n is 2, Y and Z are taken together to form a bond or a linking group of from 1 to 10 carbon atoms and from 0 to 6 heteroatoms, with from 0 to 4 heteroatoms in the chain, where the heteroatoms are N, O, and S.

2. A compound of the formula:

wherein:
$X^1$ is nitro or cyano;
$V^1$ is $CF_3$;
$A^1$ is a chalcogen other than S;
$Y^1$ is alkylene of from 2 to 8 carbon atoms;
$Z^1$ is a polyfluoroacylamido of from 2 to 8 and having at least $2m-2$ fluoro groups,
wherein m is the number of carbon atoms, or substituted arylamino of from 6 to 10 carbon atoms, and halogen of atomic number from 9 to 80.

3. A compound of the formula:

wherein:
$X^3$ is cyano;
$V^3$ is $CF_3$;
$n^3$ is 1 or 2;
$Q^3$ is a chalcogen;
when n is 1, $Y^3$ is a bond or linking group of a total of from 1 to 6 atoms, which are C, N, O, and S;
$Z^3$ is alkyl of from 1 to 6 carbon atoms, polyfluoroacylamido of from 2 to 6 carbon atoms and at least $2m-2$ fluorine atoms, wherein m is the number of carbon atoms, or haloanilino, where halo is of atomic number from 9 to 80; and
when n is 2, $Y^3$ and $Z^3$ are taken together to form a linking group of a total of 1 to 10 C, N, O, and S atoms.

4. A compound according to claim 1, wherein n is 1.

5. A compound according to claim 4, wherein Z is perfluoroacylamido.

6. A compound according to claim 1, wherein n is 2.

7. A compound according to claim 6, wherein T and $T^1$ are H and Y and Z are taken together to define a linking group of a total of from 2 to 8 carbon atoms and O, S and N heteroatoms.

8. A compound according to claim 1, wherein Z is radiolabeled with an iodine radioisotope.

9. A compound according to claim 2, wherein $Z^1$ is a polyfluoroacylamido group and $A^1$ is sulfur.

10. A compound of the formula:

wherein:
$X^2$ is nitro or cyano;
$V^2$ is $CF_3$;
$n^2$ is 1 or 2;
$U^2$ is a bond, N or chalcogen;
when n is 1, $Y^2$ is a bond or linking group of a total of from 1 to 6 atoms, which are C, N, O, and S; with the proviso that when $U^2$ is a bond, $Y^2$ is also a bond; and
$Z^2$ is polyfluoroacylamido of from 2 to 6 carbon atoms and at least $2m-2$ fluorine atoms, wherein m is the number of carbon atoms, an aliphatic group of from 1 to 6 carbon atoms substituted with a radioisotope or haloanilino, where halo is of atomic number 9 to 80; and
when n is 2, $Y^2$ and $Z^2$ are taken together to form a linking group of a total of 1 to 10 C, N, O, and S atoms.

11. A compound according to claim 10 of the formula 4-nitro-3-trifluoromethyl-N-({2'-hydroxy-2'-methyl-3'-N-heptafluorobutyramido}propionyl)aniline.

12. A compound according to claim 10 of the formula 3-({({4'-bromophenyl}amino)thiono}amino)-2-hydroxy-2-methyl-N-(4"-nitro-3"-trifluoromethyl)phenyl)propionamide.

13. A compound according to claim 10 of the formula N,N-bis-(3,3'-di{N'-3"-trifluoromethyl-4"-nitrophenyl}-2"-hydroxy-2"-methylpropionamide)amine.

14. A compound according to claim 10 of the formula N-(3'-trifluoromethyl-4'-cyano) 2-hydroxy, 2-methyl-3-perfluorobutyramidopropionamide.

15. A compound according to claim 10, wherein $Z^2$ is an aliphatic group substituted with an iodine radioisotope.

16. A compound of the formula N-(3-trifluoromethyl-4-cyanophenyl), N'-propyl thiourea.

17. A method of treating one or more symptoms of a hyper-androgenic syndrome, or cell hyperplasia, dependent upon activation of the androgen receptor, said method comprising:
administering an effective amount to inhibit said activation of a compound according to claim 1.

18. A method according to claim 17, wherein said hyper-androgenic syndrome is a hyper-androgenic skin syndrome and said administering is topical.

19. A method according to claim 17, wherein said cell hyperplasia is cancer and said administering is systemic.

20. A pharmaceutical formulation comprising a compound according to claim 1 and a pharmacologically acceptable carrier.

21. A method of treating alopecia, said method comprising:
treating a host suffering from alopecia in a pharmacologically effective amount with a combination of a compound according to claim 1 and a second, agent for treating alopecia, whereby said alopecia is alleviated.

22. A compound of the formula according to claim 1, wherein said polyfluoroacylamido group is of from 2 to 6 carbon atoms.

23. A compound of the formula according to claim 1, wherein said polyfluoroacylamido group is of from 3 to 5 carbon atoms.

24. A compound according to claim 3, wherein $X^3$ is nitro or cyano, and $Q^3$ is a chalcogen other than S.

25. A compound according to the formula of claim 10, where said compound is radioactively labeled.

26. A method of treating androgenic effluvium or alopecia, said method comprising:

treating a host suffering from alopecia with an effective therapeutic amount of a combination of a compound according to claim 10 and a second agent for treating androgenic effluvium or alopecia, whereby said androgenic effluvium or alopecia is alleviated.

27. The method according to claim 26 wherein said compound is of the formula 4-nitro-3-trifluoromethyl-N-({2'-hydroxy-2'-methyl-3"-N-heptafluorobutyramido}propionyl)aniline.

28. The method according to claim 26 wherein said compound is of the formula 3-({({4'-bromophenyl}amino) thiono}amino)-2-hydroxy-2-methyl-N-(4"-nitro-3"-(trifluoromethyl)phenyl)propionamide.

29. The method according to claim 26 wherein said compound is of the formula N,N-bis-(3,3'-di{N-3"-trifluoromethyl-4"-nitrophenyl}-2"-hydroxy-2"-methylpropionamide)amine.

30. The method according to claim 26 wherein said compound is of the formula N-(3'-triluoromethyl-4'-cyano) 2-hydroxy, 2-methyl-3-perfluorobutyramidopropionamide.

31. A compound according to claim 3 or claim 27, wherein $Z^2$ is an aliphatic group substituted with an iodine radioisotope.

32. The method according to claim 18, wherein said hyper-androgenic skin syndrome is alopecia, hirsutism, or acne vulgaris.

33. The method according to claim 19, wherein said cancer is prostate cancer.

34. The compound according to claim 1, wherein said compound is radiolabeled.

35. The compound according to claim 2, wherein said compound is radiolabeled.

* * * * *